(12) United States Patent
Cuzzato

(10) Patent No.: US 6,437,200 B1
(45) Date of Patent: *Aug. 20, 2002

(54) PROCESS FOR OBTAINING PENTAFLUOROETHANE BY CHLOROTETRAFLUOROETHANE DISMUTATION

(75) Inventor: Paolo Cuzzato, Treviso (IT)

(73) Assignee: Ausimont S.p.A, Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/568,535

(22) Filed: May 11, 2000

(30) Foreign Application Priority Data

May 13, 1999 (IT) .......................... MI99A1038

(51) Int. Cl.$^7$ ............................... C07C 19/08
(52) U.S. Cl. ...................................... 570/163
(58) Field of Search ........................ 570/163

(56) References Cited

U.S. PATENT DOCUMENTS 5,847,242 A  * 12/1998  Rao et al. .................... 570/151

FOREIGN PATENT DOCUMENTS

| EP | 0 408 005 B1 | 1/1991 |
| EP | 0 569 832 B1 | 11/1993 |
| EP | 0 569 832 A1 | 11/1993 |
| FR | 1 383 927 | 11/1963 |
| FR | 2 736 049 | 1/1997 |
| WO | WO 95/16654 | 6/1995 |

OTHER PUBLICATIONS

Derwent Publications, XP002148416, JP 01–172347, Jul. 7, 1989.
Chemical Abstracts, vol. 98, No. 25, XP002148415, "Fluoroalkanes".
Gopal et al., Recent Advances in Basic and Applied Aspects of Industrial Catalysis, Studies in Surface Science and Catalysis, vol. 113, (1998) pp. 405–417; "Effect of method of preparation on the dismutation activity of $CCl_2F_2$ over $Cr_2O_3$–MgO–$Al_2O_3$ catalysts".

* cited by examiner

Primary Examiner—Alan Siegel
(74) Attorney, Agent, or Firm—Arent Fox Kintner Plotkin & Kahn

(57) ABSTRACT

A gaseous process for obtaining pentafluoroethane by dismutation of chlorotetrafluoroethane in the presence of a supported catalyst, said catalyst being formed of a mixture of trivalent chromium oxide with at least an alkaline-earth metal oxide selected from Mg, Ca, Sr and Ba.

7 Claims, No Drawings

PROCESS FOR OBTAINING PENTAFLUOROETHANE BY CHLOROTETRAFLUOROETHANE DISMUTATION

The present invention relates to a process which allows to obtain very pure and with high yields $CHF_2$—$CF_3$ (HFC 125) pentafluoroethane.

HFC 125 is an harmless fluorocarbon for the ozone layer, therefore meeting the requirements of the Montreal Treaty. For the commercial uses of the compound an high purity is required.

The possibility to obtain pure pentafluoroethane depends on the type of impurities which are formed during the synthesis. For example CFC 115 (chloropentafluoroethane $CF_2Cl$—$CF_3$) is an impurity which can be eliminated with difficult from HFC 125, therefore its presence does not allow to obtain the compound at a very pure level. In order to produce pentafluoroethane meeting these requirements, processes must be employed wherein CFC 115 does not form or is formed only in traces.

The industrial processes to produce HFC 125 usually utilize HCFC 124 (tetrafluorochloroethane $C_2HF_4Cl$) as starting compound. HCFC 124 is subjected to fluorination with HF, on suitable catalyst, or is transformed (by dismutation) into a mixture of HFC 125+HCFC 123 (dichlorotrifluoroethane $C_2HF_3Cl_2$) by operating at a suitable temperature and in the presence of a catalyst. In the patent application WO 95/16654 a process for obtaining pentafluoroethane is described starting from a previously obtained gas mixture and containing as main component chlorotetrafluoroethane and lower amounts of chlorofluorocarbons (CFCs) with two carbon atoms. In a first step CFCs are separated, so as to have HCFC 124 substantially pure for the reaction with HF, in particular free from dichlorotetrafluoroethane ($C_2Cl_2F_4$) CFC 114, which under these conditions would react forming CFC 115. Therefore this patent discloses that in order to obtain pure HFC 125 by reacting HF with HCFC 124, the starting compound must be previously purified by removing the impurities of chloroflurocarbon $C_2$ (114).

The dismutation process of HCFC 124 is more suitable with respect to the reaction with HF since the starting compound purity is less criticl, further the selectivity is higher. This process has the drawback that the HCFC 124 conversion into HFC 125 is limited by the increase of the reaction by-products amounts. See EP 569,832 in the name of the Applicant.

The need was felt of a process for producing HFC 125 starting from HCFC 124, wherein it was possible to increase the amount of the produced HFC 125, reducing the amount of impurities in comparison with the fluorocarbon synthesis described with the known processes.

It has been surprisingly and unexpectedly found by the Applicant that it is possible to solve the above problem, and this is an object of the invention, using a gaseous process, wherein pentafluoroethane is obtained by dismutation of chlorotetrafluoroethane, in the presence of a catalyst comprising a mixture of trivalent chromium oxide with at least an alkaline-earth metal oxide selected from Mg, Ca, Sr and Ba.

The reaction temperature is in the range 150° C.–250° C., preferably 180° C.–240° C.

The contact time with the catalyst, determined as the ratio between the catalyst volume and that of the gas flow at the working temperature and pressure is in the range 5–30 seconds, preferably 10–20 seconds.

The pressure is not critical, but preferably is comprised between 1 and 10 bar.

The reaction is carried out by flowing gaseous HCFC 124, optionally diluted with an inert gas such as for example nitrogen, through the catalyst.

Preferably the reaction is carried out in a fluidized bed; in this case the catalyst particles must have sizes suitable for this kind of plant.

The g atoms ratio between the chromium and the alkaline-earth metals ranges from 50:1 to 3:1, preferably from 20:1 to 5:1.

The catalyst is preferably supported.

Preferably the catalyst support is aluminum fluoride obtainable by alumina fluorination, and having a fluorine content not lower than 90%, preferably not lower than 95%, with respect to the stoichiometric.

Generally the used $AlF_3$ is mainly formed of gamma phase, as described in FR 1,383,927, and has a surface area generally in the range 25–35 $m^2/g$. If the catalyst is used in a fluidized bed the support has the granulometry suitable for this kind of reactor, as well known to the skilled in the field.

In the supported catalyst the sum of the percentages of the contained chromium and alkaline-earth metal is in the range 5–15% by weight, preferably 10–15%.

The catalyst is preferably prepared by impregnation of the support with an aqueous solution of a soluble chromium and of the alkaline-earth metals salt. The support impregnation can be carried out with any method known in the prior art, for example with the method known as dry impregnation, for example as described in EP 408,005, herein incorporated by reference.

According to this method the impregnation is carried out by pouring on the support, in sequence, according to the process described hereinunder, portions of an impregnating solution, such that the global volume is not higher than the volume of the aluminum fluoride pores. The solution for the impregnation is prepared by dissolving in water the required amounts of the corresponding salts, preferably chlorides, of the trivalent chromium and of the alkaline-earth metals. The solution is poured in portions on the support, drying at 110° C. for some hours after every addition, in order to evaporate the water from the support pores.

At the end of the impregnation, the catalyst must be activated: the operation can be directly carried out in the reactor used for the dismutation, by calcining in inert gas current, at the temperature of about 400° C. for 4–8 hours and then treating at 360° C. with anhydrous HF for 12–24 hours.

Some Examples are given for illustrative purposes and they are not limitative of the employment possibility of the invention.

EXAMPLE 1A

Preparation of a Chromium/Calcium/$AlF_3$ Catalyst 400 g of aluminum fluoride having pore volume of 0.25 cc/g, and granulometry suitable to the use in a fluidized bed, are impregnated again and again with a total of 240 cc of aqueous solution, containing 252.5 g of $CrCl_3 \cdot 6H_2O$ and 7.7 g of anhydrous $CaCl_2$, and subsequently activated as above described.

The so prepared catalyst contains 10% by weight of chromium and 0.5% by weight of calcium.

EXAMPLE 1B

Dismutation of 124 on the Chromium-Calcium Catalyst of Example 1A at the Temperature of 200° C.

350 g of the catalyst prepared according to Example 1A are placed in a 5 cm tubular Inconel® 600 reactor, equipped with porous septum at its base and electrically heated. The catalyst is heated up to 200° C. in nitrogen flow. At this temperature 2 moles/hour (273 g/h) of a mixture of about $^{95}/_5$ by moles of the HCFC 124 and HCFC 124a isomers are fed. The gases coming out from the reactor are washed in water to absorb acidity traces, and analyzed by gaschromatography with thermoconductivity detector. The results of the gaschromatographic analysis on the reaction mixture are reported in Table 1.

From the Table it results that the HCFC 124 conversion is equal to 59.7% and that the yield in HFC 125 (defined as produced 125/reacted 124) is 51.4%. The produced HFC 125 moles/hour are 0.61. The specific productivity of the produced HFC 125 (grams) in the time unit/weight of catalyst is over 210 (g/Kg catalyst)/hour. The CFC 115 content in the reaction mixture is lower than the detectability limit of the gaschromatographic method (about 100 ppm). The analysis of this impurity is repeated by GC-MS, but it results unmeasurable since still lower than the detectability limit (1 ppm).

HCFC 124 and 1110 are recycled in the process. Therefore the latter is not considered a process impurity.

EXAMPLE 1C
Dismutation of HCFC 124 on the Chromium-Calcium Catalyst of Example 1A at the Temperatures of 220° and 240° C. Respectively The dismutation reaction is repeated, following the process described in the previous Example 1B, at the temperatures of 220° C. and 240° C. respectively.

The results are reported in Table 1.

From the Table it is noted that the CFC 115 amount at the temperature of 220° is unmeasurable with the thermoconductivity detector, and that also at the temperature of 240° C. the CFC 115 amount remains lower than 100 ppm. At this temperature the HCFC 124 conversion is of about 80% and the yield as above defined is 54.7%. The produced HFC 125 moles/hour are 0.87. Therefore the specific productivity at 240° C. of the produced HFC 125 (grams) in the time unit/weight of catalyst is of about 300 (g/Kg catalyst)/hour.

EXAMPLE 2A
Preparation of a Chrome-Strontium/$AlF_3$ Catalyst 400 g of aluminum fluoride, having pore volume of 0.25 cc/g, with granulometry suitable to the use in a fluidized bed, are impregnated again and again with a total volume of 240 cc of aqueous solution containing 264 g of $CrCl_3 \cdot 6H_2O$ and 15.7 g of $SrCl_2 \cdot 6H_2O$, and subsequently activated as described in the catalyst preparation method. The so prepared catalyst contains 10% by weight of chromium and 1% by weight of strontium.

EXAMPLE 2B
Dismutation of HCFC 124 on the Chromium-Strontium Catalyst of Example 2A at the Temperature of 220° C.

300 g of catalyst prepared according to Example 2A are placed in the previously described tubular reactor and heated to 220° C. in nitrogen flow. When this temperature is reached, 2 moles/hour (273 g/h) of a nearly $^{95}/_5$ mixture of the HCFC 124 and HCFC 124a isomers are fed. The gases coming out from the reactor are washed in water to absorb acidity traces, and analyzed by gaschromatography. The results are reported in Table 1.

From the Table it results that the conversion of HCFC 124 is 55.8%. The yield is 51.2%. The produced HFC 125 moles/hour are 0.57. The specific productivity as above defined is 228 (g/Kg catalyst) /hour. The CFC 115 content is unmeasurable with the thermoconductivity detector. The analysis repeated by GC-MS gives a CFC 115 amount of about 55 ppm. The CFC 115/HFC 125 ratio is lower than 200 ppm.

EXAMPLE 2C
Dismutation of HCFC 124 on the Chromium-Strontium Catalyst of Example 2A at the Temperature of 240° C.

The test of Example 2B is repeated at the temperature of 240° C.

The results are reported in Table 1, from which it results that at 240° C. the formed CFC 115 amount is 100 ppm, the conversion of HCFC 124 is 68.5% and the yield is 52.7%.

The produced HFC 125 moles/hour at this temperature are 0.72. The specific productivity of 125 is therefore 289 (g/Kg catalyst)/hour.

EXAMPLE 3A
Preparation of a Chromium/Magnesium/$AlF_3$ Catalyst 500 g of aluminum fluoride having a pore volume equal to 0.25 cc/g, with granulometry suitable to the use in a fluidized bed, are impregnated again and again with a total volume of 327 cc of aqueous solution containing 327 g of $CrCl_3 \cdot 6H_2O$ and 50 g of $MgCl_2 \cdot 6H_2O$. The catalyst is subsequently activated as previously described. The so prepared catalyst contains 10% by weight of chromium and 0.9% by weight of magnesium.

EXAMPLE 3B
Dismutation of HCFC 124 on the Chromium-Magnesium Catalyst of Example 3A at the Temperature of 220° C.

300 g of the catalyst prepared according to Example 3A are placed in the previously described tubular reactor and heated to 220° C. in nitrogen flow. When the catalyst is stabilized at this temperature, 2 moles/hour (273 g/h) of a nearly $^{95}/_5$ (molar ratio) mixture of the HCFC 124 and HCFC 124a isomers are fed. The gases coming out from the reactor are washed in water to absorb acidity traces, and analyzed by gaschromatography. The following results are obtained:

125 31.4% moles
124 38.3% moles
123 29.9% moles
others 0.4% moles

The HCFC 124 conversion is equal to 61.7%. The yield as above defined is 50.9%. The produced HFC 125 moles/hour are 0.63. The CFC 115/HFC 125 ratio is 100 ppm (GC-MS analysis). The specific productivity of the 125 is 251 (g/Kg catalyst)/hour.

EXAMPLE 4A (Comparative)
Preparation of a Chromium/$AlF_3$ Catalyst 400 g of aluminum fluoride having a pore volume 0.25 cc/g, and granulometry suitable to the use in a fluidized bed, are impregnated again and again with a total volume of 420 cc of aqueous solution, containing 275 g of $CrCl_3 \cdot 6H_2O$ and subsequently activated as above described.

The so prepared catalyst contains 10.5% by weight of chromium.

EXAMPLE 4B (Comparative)
Dismutation Reaction of HCFC 124 on the Catalyst of Example 4A at the Temperatures of 180° C., 220° C., 240° C., 260° C. 280° C., 300° C. and 320° C. Respectively About 400 g of the catalyst prepared according to Example 4A are placed in the previously described tubular reactor and heated to the reaction temperature in nitrogen flow. When the catalyst is in temperature, 2 moles/hour (273 g/h) of a nearly $^{95}/_5$ mixture of the HCFC 124 and HCFC 124a isomers are fed. The gases coming out from the reactor are washed in water to absorb acidity traces and analyzed by gaschromatography. The results obtained at the various temperatures are reported in Table 2.

From the Table it results that at the temperature of 180° C. the 124 conversion is 43.5%. The produced HFC 125 moles/hour are 0.45. The specific productivity is 135 (g/Kg catalyst)/hour. The content of 115 in 125, determined by GC, results <100 ppm.

By using the same above described experimental conditions, reactions at 220° C., 240° C., 260° C., 280° C., 300° C. and 320° C. are carried out, in order to increase the conversion.

From Table 2 it results that by operating at temperatures higher than 220° C., the obtained HFC 125 moles/hour increase but the $^{115}/_{125}$ ratio has very high values starting from the temperature of 240° C. (0.13%). By lowering the temperature to improve the product purity also the specific productivity decreases. For example at the temperature of 220° C. the 124 conversion is 52.8% with an yield in 125 of 51%. Therefore the specific productivity of 125 is about 161 g/Kg catalyst/hour.

TABLE 1

Dismutation reaction of HCFC 124 on chromium/calcium and chromium/strontium catalyst at the temperatures of 200° C., 220° C. and 240° C. In the Table 123 and 124 are the mixtures of the possible isomers. In the Table the specific productivity of 125 is indicated with S.P.$_{125}$

| compound | Cr/Ca Catalyst (Ex. 1A) | | | Cr/Sr Catalyst (Ex. 2A) | |
|---|---|---|---|---|---|
| | Temperatures (° C.) | | | | |
| | 200 (Ex. 1B) | 220 (Ex. 1C) | 240 (Ex. 1C) | 220 (Ex. 2B) | 240 (Ex. 2C) |
| | % moles | | | | |
| 125 | 30.67 | 30.74 | 43.78 | 28.58 | 36.08 |
| 115 | 0.00 | 0.00 | 0.01 | 0.00 | 0.01 |
| 124 | 40.33 | 39.55 | 20.02 | 44.22 | 31.50 |
| 133 | 0.00 | 0.01 | 0.05 | 0.16 | 0.14 |
| 114 | 0.01 | 0.02 | 0.04 | 0.04 | 0.07 |
| 123 | 28.72 | 29.38 | 34.79 | 26.76 | 31.48 |
| 1110 | 0.18 | 0.14 | 1.00 | 0.10 | 0.36 |
| others | 0.09 | 0.15 | 0.31 | 0.12 | 0.30 |
| convers. 124 % moles | 59.67 | 60.45 | 79.98 | 55.78 | 68.50 |
| 125 moles/h obtained | 0.61 | 0.62 | 0.87 | 0.57 | 0.72 |
| S.P.$_{125}$ | 210 | 212 | 300 | 228 | 289 |
| 115/125 % moles | <1 ppm in the crude product | <100 ppm in the crude product | 0.02 | 0.02 | 0.03 |

TABLE 2

Ex. 4B - comparative: Analysis of the gases contained in the reaction mixture obtained by dismutation of HCFC 124 in the presence of a Cr$^{III}$/ALF$_3$ catalyst at the temperatures of 180° C., 220° C., 240° C., 260° C., 280° C., 300° C. and 320° C. respectively.
S.P.$_{125}$ has the same meaning of Table 1.

| Compound % moles in the mixture | Temperatures (° C.) | | | | | | |
|---|---|---|---|---|---|---|---|
| | 180 | 220 | 240 | 260 | 280 | 300 | 320 |
| 125 | 22.36 | 27.01 | 39.80 | 45.02 | 50.69 | 50.28 | 52.15 |

TABLE 2-continued

Ex. 4B - comparative: Analysis of the gases contained in the reaction mixture obtained by dismutation of HCFC 124 in the presence of a Cr$^{III}$/ALF$_3$ catalyst at the temperatures of 180° C., 220° C., 240° C., 260° C., 280° C., 300° C. and 320° C. respectively.
S.P.$_{125}$ has the same meaning of Table 1.

| Compound % moles in the mixture | Temperatures (° C.) | | | | | | |
|---|---|---|---|---|---|---|---|
| | 180 | 220 | 240 | 260 | 280 | 300 | 320 |
| 115 | 0.00 | 0.00 | 0.05 | 0.16 | 0.51 | 0.95 | 2.43 |
| 124 | 58.50 | 47.20 | 25.53 | 21.77 | 18.57 | 19.15 | 18.22 |
| 133 | 0.03 | 0.06 | 0.16 | 0.31 | 0.65 | 1.07 | 2.23 |
| 114 | 0.02 | 0.07 | 0.10 | 0.16 | 0.23 | 0.44 | 0.69 |
| 123 | 21.07 | 25.49 | 33.39 | 31.48 | 27.96 | 26.31 | 22.13 |
| 1110 | 0.00 | 0.05 | 0.68 | 1.08 | 0.72 | 0.60 | 0.55 |
| Others | 0.02 | 0.11 | 0.28 | 0.04 | 0.67 | 1.19 | 1.6 |
| Conv. 124 | 41.50 | 52.80 | 74.47 | 78.23 | 81.43 | 80.85 | 81.78 |
| 125 moles/h | 0.45 | 0.54 | 0.79 | 0.90 | 1.01 | 1.00 | 1.04 |
| S.P.$_{125}$ | 135 | 161 | 236 | 269 | 304 | 302 | 313 |
| 115/125 % moles | <100 ppm in the crude product | <100 ppm in the crude product | 0.13 | 0.36 | 1.01 | 1.88 | 4.67 |

What is claimed is:

1. A gaseous process for obtaining pentafluoroethane by dismutation of chlorotetrafluoroethane, in the presence of a catalyst comprising a mixture of trivalent chromium oxide with at least an alkaline-earth metal oxide selected from Mg, Ca, Sr and Ba, wherein the g atoms ratio between the chromium and the alkaline-earth metals ranges from 50:1 to 3:1.

2. A process according to claim 1, wherein the reaction temperature is in the range 150° C.–250° C.

3. A process according to claims 1, wherein the contact time with the catalyst is in the range 5–30 seconds.

4. A process according to claims 1, wherein the catalyst is supported.

5. A process according to claim 4, wherein the support is aluminum fluoride obtainable by alumina fluorination, having a fluorine content not lower than 90% preferably not lower than 95% with respect to the stoichiometric.

6. A process according to claim 5, wherein the aluminum fluoride is mainly formed of gamma phase and has a surface area generally in the range 25–35 m$^2$/g.

7. A process according to claim 4, wherein in the supported catalyst the sum of the percentages of the contained chromium and alkaline-earth metals is in the range 5–15% by weight preferably 10–15%.

* * * * *